United States Patent [19]

Dye

[11] Patent Number: 5,122,369

[45] Date of Patent: Jun. 16, 1992

[54] NUTRIENT COMPOSITION FOR PREVENTING HAIR LOSS

[75] Inventor: R. Harvey Dye, Santa Barbara, Calif.

[73] Assignee: Harmony Health Products, Inc., Santa Barbara, Calif.

[21] Appl. No.: 686,312

[22] Filed: Apr. 16, 1991

Related U.S. Application Data

[63] Continuation of Ser. No. 503,384, Mar. 30, 1990, abandoned.

[51] Int. Cl.$^5$ .................. A61K 33/00; A61K 33/26
[52] U.S. Cl. ........................ 424/646; 424/401; 424/464; 424/600; 424/648; 424/667; 514/356; 514/387; 514/566; 514/784; 514/880
[58] Field of Search .............. 424/464; 514/23, 566, 514/167

[56] References Cited

U.S. PATENT DOCUMENTS

| | | | |
|---|---|---|---|
| 4,454,125 | 6/1984 | Demopoulos | 514/903 |
| 4,743,442 | 5/1988 | Raaf | 514/167 |
| 4,814,351 | 3/1989 | Mathews | 514/566 |
| 4,871,550 | 10/1989 | Millman | 514/23 |

*Primary Examiner*—Thurman K. Page
*Assistant Examiner*—James M. Spear
*Attorney, Agent, or Firm*—Michael G. Petit

[57] ABSTRACT

An orally acceptable nutrient and mineral supplement for reducing hair loss wherein the composition contains divalent iron and pantothenic acid in a weight to weight ratio of approximately 1-3 and racemic d, 1-methionine. A particularly preferred composition contains 11.25 mg. of divalent iron as ferrous fumarate and 35 mg. of pantothenic acid as calcium pantothenate and 200 mg. of d,1-methionine.

2 Claims, No Drawings

NUTRIENT COMPOSITION FOR PREVENTING HAIR LOSS

CROSS REFERENCE TO RELATED APPLICATIONS

This is a continuation of application Ser. No. 07/503,384, filed Mar. 30, 1990, abandoned.

BACKGROUND OF THE INVENTION

1. Field of the Invention

This invention relates to a novel orally acceptable vitamin and mineral composition containing pantothenic acid, methionine and iron which is effective in decreasing hair loss.

2. Prior Art

A man normally in his early twenties has approximately 100,000 to 150,000 hairs on his scalp. It is normal to lose 50 to 100 hairs daily. The maintenance of this normal number of hairs depends on a cycle called the pilar cycle. The pilar cycle governs the steps in which the hair is formed, grows and falls before being replaced by a new part in the same follicle.

In the course of a pilar cycle, three successive phases are observed: the anagen phase, the catagen phase and the telogen phase. During the first phase, referred to as the anagen phase, the hair passes through an active growth period associated with intense metabolic activity in the bulb region. The second phase, referred to as the catagen phase, is transitory and is marked by a slowing down of metabolic activities. During this phase, the hair undergoes an involution, the follicle atrophies and the hair's implantation in the skin appears increasingly shallow. The final phase, referred to as the telogen phase, corresponds to a rest period for the follicle and the hair finally falls out pushed by a new formed anagen hair. This constant physical renewal process undergoes a natural change during aging. The hair decreases in diameter and the pilar cycle becomes shorter.

When the cyclic nature of this process becomes unbalanced, that is, when the generation of new anagen bulbs is delayed with respect to the entry of bulbs into catagen and telogen states, hair loss occurs. Balding, therefore, is a result of many cycles of hair growth out of balance, which is characterized by gradual diminution of the number of anagen bulbs over successive cycles. It is reasonable to assume that if hair follicles can be maintained in the active anagen state for a longer period, there will be less hair loss as follicles pass to catagen and telogen states. The fewer bulbs lost in the normal progression of hair follicles, the fewer new bulbs need to take their place.

The pilar cycle appears to depend on at least three factors which may produce baldness. These include nutritional factors, endocrinal factors, and a nervous factor related to stress.

Compositions which enable baldness to be eliminated or reduced either by stimulating or inducing hair growth or reducing hair loss have been sought in the cosmetic and pharmaceutical industry for many years.

One approach to the problem of hair loss contends that "unplugging" the hair follicle will result in more luxuriant hair growth. This view suggests that the hair follicle is "strangled" by buildup of sabacious secretions in the pilary canal. Treatment of this microscopic strangulation with products containing waxes or fatty acid esters, such as polysorbate 60 or polysorbate 80, followed by peeling has gained some popularity but there is no scientific evidence to support effectiveness of waxing/peeling in stimulating hair growth.

More recently interest in hair loss has been rekindled by the promise of topically applied drugs such as Rocaine (Upjohn), which in some cases support hair regrowth in balding persons. The mechanisms of actions of these drugs and their safety and effectiveness are under study.

Histochemical studies of hair follicles show that anagen follicles differ from catagen and telogen follicles with respect to the presence of calcium ions. The average calcium content of anagen bulbs is the order of one nanogram per bulb. The average calcium content of catagen bulbs appears to be about twice as high whereas the calcium content of telogen bulbs appears to average about four nanograms per bulb although calcium concentrations as high as twenty nanograms per bulb has been demonstrated in some telogen bulbs. Villus follicles, that is, the follicles containing the diminutive non-growing, non-pigmented incompletely keratinized hair characteristic of the bald scalp, have a relatively high concentration of calcium ions when compared with "normal" hair follicles. This is the common "peach fuzz" appearance of the scalp on bald persons. It remains unclear whether the relatively high calcium ion concentration in villus and telogen follicles are a cause or a result of these follicles inability to reenter the anagen phase.

These observations have led to the development of a composition that has at least one active ingredient consisting essentially of active chelating agents. The ability of such compositions to chelate divalent calcium ions is generally credited to be responsible for their efficacy. Such compositions are distributed on the scalp and left in place at least eight hours. Preferably such applications are made daily for at least the first month of treatment. The effectiveness of chelating agents such as EDTA in slowing down hair loss seems to support the theory that baldness and increasing hair loss is associated with increase in calcium ion in the telogen bulbs.

SUMMARY OF THE INVENTION

There is provided in practice of this invention according to a presently preferred embodiment, a novel nutrient composition which decreases the rate of hair loss in many individuals susceptible to such loss. Such a treatment comprises daily oral consumption of an orally acceptable composition comprising divalent iron and pantothenic acid in a weight/weight ratio of about 1:3 and d,l-methionine in an amount sufficient to effect reduction of the rate of hair loss.

It is one object of this invention to provide a safe orally acceptable nutrient supplement which can delay the normal rate of conversion of active anagen bulbs to metabolically inactive catagen bulbs. It is desirable that such a composition decrease the rate of shedding of hair. It is desirable that such a composition employ inexpensive, harmless nutrients and may be taken orally by individuals without professional assistance or counseling.

DESCRIPTION OF THE PREFERRED EMBODIMENT

The oral daily ingestion of a composition comprising d,l-methionine, pantothenic acid and divalent iron is effective at reducing the rate of hair loss in some individuals. The preferred composition of a daily dose according to this invention contains between 8 and 12 mg. (preferably 11.25 mg) of iron in the divalent form as ferrous fumarate and 35 mg of pantothenic acid as dicalcium pantothenate and 150-200 mg of d,1-methionine in an inert orally acceptable filler. Other ingredients preferably include folic acid, niacin, biotin, iodine, inositol, p-amino benzoic acid, and l-lysine in amounts corresponding to the recommended daily allowance established by the U.S. Food and Drug Administration.

What I claim is:

1. A composition which, when consumed daily, is effective for reducing the rate of hair loss in certain individuals consisting essentially of between 8-12mg of divalent iron, 35mg of pantothenic acid and between 150-200mg of d,1-methionine in an inert orally acceptable filler.

2. A composition which, when consumed daily, is effective for reducing the rate of hair loss in certain individuals consisting essentially of between 8-12 mg of divalent iron, 35 mg of pantothenic acid, between 150-200 mg of d,1-methionine and folic acid, niacin, biotin, iodine, inositol, p-amino benzoic acid and l-lysine in amounts corresponding to the recommended daily allowance in an orally acceptable filler.

* * * * *